United States Patent
Beat et al.

[11] Patent Number: 6,155,991
[45] Date of Patent: Dec. 5, 2000

[54] APPARATUS AND METHOD FOR COLLECTING BLOOD SAMPLES

[75] Inventors: Thomas R. Beat; Conrad H. Boettger; Joe A. Carrithers, all of Wichita, Kans.

[73] Assignee: Via Christi Research, Inc., Wichita, Kans.

[21] Appl. No.: 09/345,486

[22] Filed: Jul. 1, 1999

[51] Int. Cl.$^7$ ...................................................... A61B 5/00
[52] U.S. Cl. .............................................................. 600/573
[58] Field of Search .................................. 600/573, 576, 600/577, 579

[56] References Cited

U.S. PATENT DOCUMENTS

| | | | |
|---|---|---|---|
| 4,214,874 | 7/1980 | White ........................................ | 23/230 |
| 4,263,922 | 4/1981 | White ........................................ | 128/763 |
| 4,466,446 | 8/1984 | Baidwan et al. ......................... | 128/765 |
| 4,521,975 | 6/1985 | Bailey ....................................... | 34/5 |
| 4,572,210 | 2/1986 | McKinnon ............................... | 128/765 |
| 4,687,000 | 8/1987 | Eisenhardt et al. ..................... | 128/760 |
| 4,979,515 | 12/1990 | Briggs et al. ........................... | 128/760 |
| 5,086,780 | 2/1992 | Schmitt .................................... | 128/763 |
| 5,514,119 | 5/1996 | Curtis ....................................... | 504/319 |
| 5,807,344 | 9/1998 | Iwasaki .................................... | 604/190 |

OTHER PUBLICATIONS

Jacky Q. Duchamp; Stephen M. Koch, Richard D. McNary and Mark Nguyen, "New Arterial Micropuncture", The Journal for Respiratory Care Practitioners, Feb./Mar. 1997.

B–D Drihep–Plus Kit, Becton Dickinson and Company, Franklin Lakes, NJ 07417.

*Primary Examiner*—Cary O'Connor
*Assistant Examiner*—Pamela Wingood
*Attorney, Agent, or Firm*—Nixon Peabody LLP; Marc S. Kaufman

[57] ABSTRACT

A small volume blood collection apparatus and method. A capillary tube has an end cap on each end thereof. Each end cap has a passage formed therethrough, a plug for selectively closing the passage and a flexible arm extending between the plug and a base portion of the end cap. A Luer surface is defined on each end cap.

26 Claims, 2 Drawing Sheets

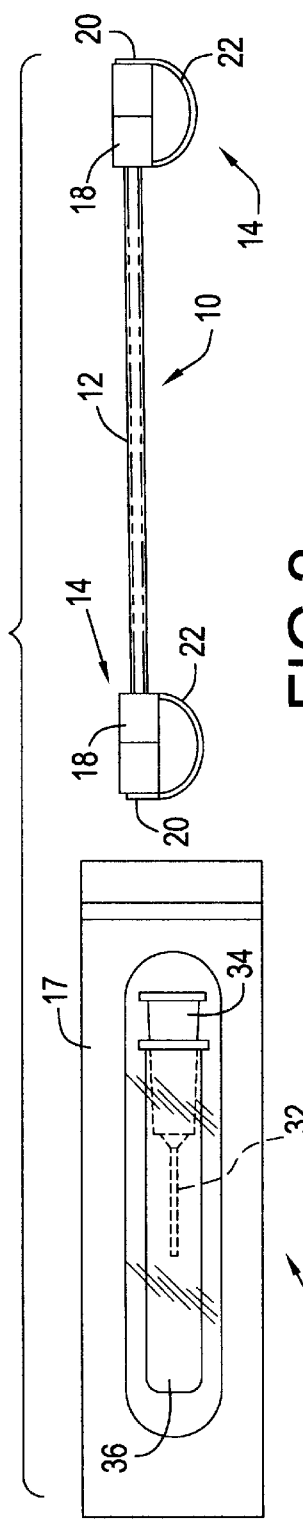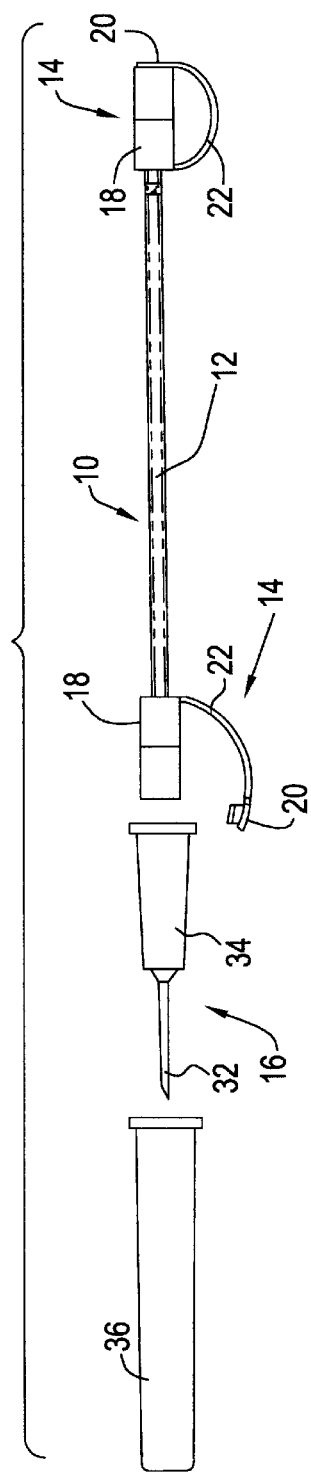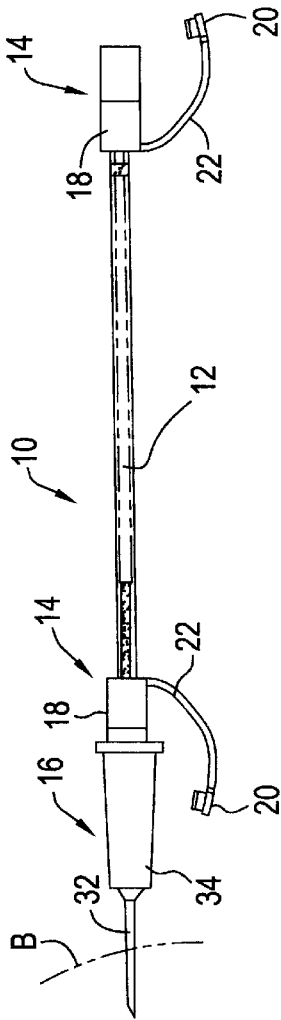

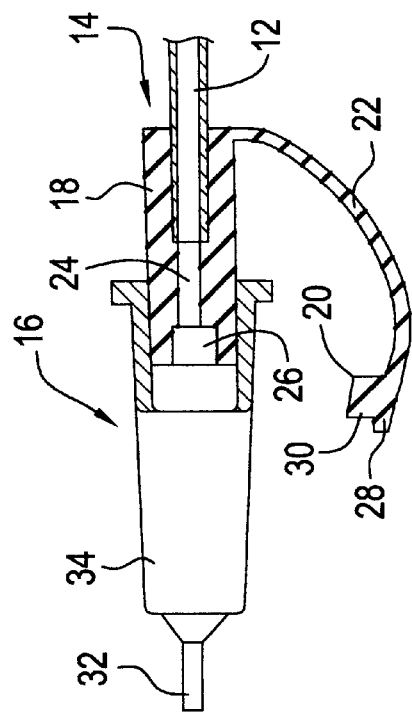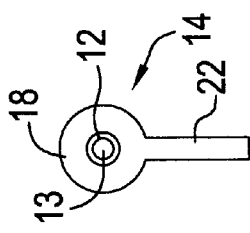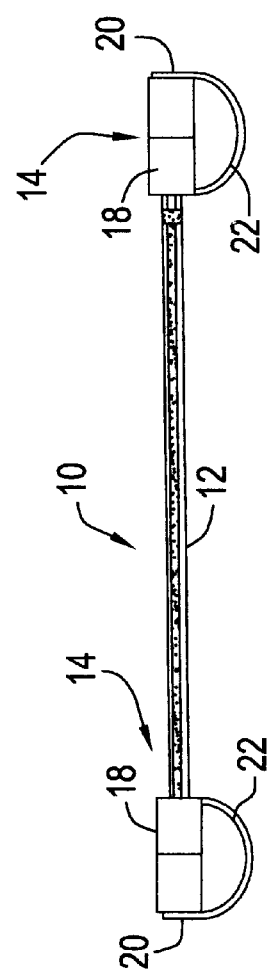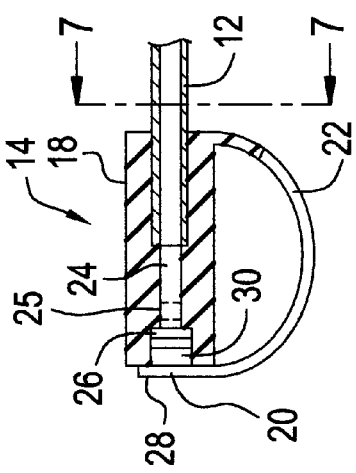

APPARATUS AND METHOD FOR COLLECTING BLOOD SAMPLES

BACKGROUND OF THE INVENTION

1. Field of the Invention

The invention relates to the collection of blood samples for testing. More particularly, the invention relates to an apparatus and method for collecting small volume blood samples while minimizing exposure of the blood samples to ambient air.

2. Description of the Related Art

It is well known to utilize syringes having a movable plunger for collecting blood samples. Syringes have proven to be effective, reliable and safe for collecting blood samples of relatively large volumes. Once a blood sample is collected, it can be introduced into various testing apparatus commonly referred to as "analyzers" for blood gas, co-oximetry, electrolyte, and metabolite analysis, for example. Recently, analyzers have been developed that are capable of accurately analyzing blood samples ranging in volume from 90–250 microliters. Syringes cannot effectively collect samples of such a small volume and thus the use of syringes for collecting blood often results in the collection of excess blood.

In many procedures, such as performing blood gas analyses in neonates, it is desirable to minimize the volume of collected blood samples. Of course, neonates have a very small blood volume. Also, blood gas analysis requires that blood be drawn at frequent intervals. Therefore, it is important to draw samples that are as small as possible to reduce or eliminate blood waste and the potential need for blood transfusions.

U.S. Pat. No. 4,263, 922 is exemplary of patents disclosing instruments and methods capable of drawing small volume blood samples. The instrument disclosed in U.S. Pat. No. 4,263,922 includes a capillary tube, a handle, and a needle assembly. The handle serves as a needle assembly adaptor for coupling the needle assembly to the tube. Blood is drawn through the needle assembly and handle into the tube via capillary action. Subsequently, the needle assembly and the handle are removed from an end of the tube and a separate cap is fitted over each end of the tube to retain the sample in the tube. Since the needle assembly and the handle must both be removed before a cap can be placed over an end of the tube, the collected blood sample is exposed to ambient air for a relatively long period of time while the end of the tube is completely open prior to fitting a cap thereto. Such exposure can negatively affect the accuracy of blood analysis on the sample because of gas exchange due to diffusion. A similar exposure to ambient air occurs when removing the caps and interfacing the tube to a blood analyzer. Also, blood may drip out of the tube in the long period of time that the tube end is open. This can reduce the accuracy of blood analysis and can present issues of disease transmission to medical personnel collecting and otherwise handling the blood sample.

SUMMARY OF THE INVENTION

It is an object of the invention to overcome the above-noted limitations of conventional instruments and methods.

It is another object of the invention to reliably collect small volume blood samples.

It is another object of the invention to collect small volume blood samples and deliver the same to a blood analyzer while minimizing exposure of the blood samples to ambient air.

It is another object of the invention to increase the accuracy of blood sample collection and analysis.

It is another object of the invention to reduce the number of parts required for a blood collection instrument.

To achieve the above object, a first aspect of the invention is a blood sample collection apparatus comprising an elongated capillary tube having an open proximal end and an open distal end, a first end cap including a base portion having an inner end and an outer end, a passage extending between the inner end and the outer end, and a plug configured to selectively close the passage, and a second end cap coupled to the distal end of the capillary tube. The inner end of the base portion of the first end cap is coupled to the proximal end of the capillary tube. A Luer surface is defined on an outer portion of the first end cap.

A second aspect of the invention is a blood sample collection method comprising the steps of coupling a needle assembly to an open proximal end of an elongated capillary tube having a first end cap thereon, the first end cap including a base portion having an inner end coupled to the proximal end of the capillary tube, an outer end, a passage extending between the inner end and the outer end, a Luer surface defined thereon, and a first plug configured to selectively close the passage. The coupling step includes disposing a hub of the needle over the Luer surface defined on the base portion with the plug not closing the opening of the passage. The method also comprises the steps of placing an end of the needle in communication with a blood supply, drawing blood through the needle and the passage into the capillary tube, closing the distal end of the capillary tube with a second end cap, removing the needle assembly from the capillary tube, and closing the passage with the plug.

A third aspect of the invention is an end cap for closing an end of a capillary tube configured to retain a blood sample. The end cap comprises a base portion having a passage defined therethrough, a plug configured to selectively close the passage, and a Luer surface defined on an outer portion of the base portion.

BRIEF DESCRIPTION OF THE DRAWING

The invention is described herein through preferred embodiments with reference to the attached drawing in which:

FIG. 1 is a side view of a blood collection apparatus in accordance with a preferred embodiment of the invention;

FIG. 2 is an exploded view of the preferred embodiment;

FIG. 3 is a side view of the preferred embodiment illustrating the drawing of blood from a blood supply;

FIG. 4 is a side view of the preferred embodiment illustrating the sealing thereof after drawing blood;

FIG. 5 is an enlarged view, in partial section of a portion of the preferred embodiment with a needle assembly attached;

FIG. 6 is is an enlarged view, in partial section of a portion of the preferred embodiment with a needle assembly removed; and FIG. 7 is a sectional view taken along line 7—7 of FIG. 6.

DETAILED DESCRIPTION OF THE PREFERRED EMBODIMENT

FIGS. 1 & 2 illustrate blood sample collection apparatus 10 in accordance with a preferred embodiment of the invention. Collection apparatus 10 includes capillary tube 12 which is a hollow elongate tube having open ends and passage 13 (see FIG. 7) therethrough, a pair of end caps 14 for selectively closing the open ends of capillary tube 12, and needle assembly 16 adapted to be coupled to capillary tube 12. Needle assembly 16 can be a conventional needle assembly and is discussed in greater detail below. Needle assembly 16 can be provided as part of apparatus 10 or separately in package 17 as illustrated in FIG. 1, and thus the phrase "blood sample collection apparatus" as used herein refers to an apparatus with or without a needle assembly. Capillary tube 12 of the preferred embodiment is proportioned to hold 100 microliters of blood in passage 13. Of course, Capillary tube 12 can be proportioned to hold any volume of blood desirable for a sample.

Capillary tube 12 can be of a known construction and can be formed of a polycarbonate material with a cellulose propionate coating on its interior surfaces. Alternatively, capillary tube 12 can be made of any suitable non-gas permeable copolymer. Capillary tube 12 can be formed by extrusion, molding, or any other appropriate process. Further, a coating of sodium heparin or advanced heparin can be formed on surfaces of capillary tube 12, or impregnated in capillary tube 12, to prevent clotting of blood contained in capillary tube 12. For example, 5 USP/microliter dried sodium heparin can be used.

End caps 14 can be formed of medical grade silicone or any other appropriate material. Preferably, end caps 14 are somewhat resilient and impervious to fluids. End caps 14 can be formed through an injection molding process or by any other appropriate method. Each end cap 14 includes base portion 18, plug 20 in the form of a stopper, and flexible arm 22 coupling plug 20 to base portion 18. Flexible arm 22 serves to captivate plug 20 with respect to base portion 18 while permitting plug 20 to selectively close an end of base portion 18 as described in detail below. As best illustrated in FIG. 6, which shows one of end caps 14 in cross-section, base portion 18 is generally tubular and has passage 24 extending therethrough. The inside diameter of passage 24, in an undeformed state, is preferably slightly less than an outer diameter of capillary tube 12. Accordingly, an end of capillary tube 12 can be inserted into passage 24 of an inner end of the base portion 18 and secured therein through a pressure fit due to resiliency of end cap 14. The relative sizes and materials of end cap 14 and capillary tube 12 can be adjusted to provide the desired frictional force to prevent undesirable separation of end cap 14 from capillary tube 12 during use and handling. Alternatively, end caps 14 can be coupled to capillary tube 12 with adhesives, fittings, or any other appropriate mechanism.

Opening 26 is formed in an outer end of base portion 18 opposite the inner end of base portion 18 that receives and end of capillary tube 12. Opening 26 is in communication with passage 24 and is adapted to receive tapered portion 30 of plug 20. When tapered portion 30 is received in opening 26, flange portion 28 of plug 20 abuts the outer end of base portion 18. Plug 20 of the preferred embodiment is in the form of a stopper. However, the plug can be configured in any manner to selectively close opening 26 and passage 24 and thus the term "plug" as used herein refers to any device for selectively closing passage 24. Including devices which close passage 24 in only one direction, or with respect to only selected fluids. For example, plug 20 can be a valve positioned in or on base portion 18, a hydrophobic filter, a selective membrane, an element defining a tortuous path, a combination of these elements or any other form of closure member 25 illustrated with a dotted line in FIG. 6. Alternatively, the plug can be a stopper in combination with a filter or other closure member. End cap 14 having a filter or other closure member can include a visual indicator, such as a colored marking or the like.

As best illustrated in FIG. 5, the outer surface of at least a portion of base portion 18 is tapered to define a Luer surface. The phrase "Luer surface", as used herein, refers to a tapered surface that will mate tightly with a complimentary surface, as defined by a needle assembly for example, such as the tapered surface described in Federal Specification GG-N-196, the disclosure of which is incorporated herein by reference. For example, the Luer surface can define an angle of approximately 1°43"6" measured from the longitudinal axis of base portion 18. The Luer surface can be formed on any portion of end cap 14.

As noted above, needle assembly 16 can be conventional in construction and includes hollow needle 32 and hub 34 made of a synthetic resin or the like. Hub 34 defines an inner Luer surface that compliments the Luer surface defined on base portion 18 to allow base portion 18 to fit snugly in hub 34, as illustrated in FIGS. 3 and 5, to couple capillary tube 12 to needle assembly 16. Removable cover 36 can be provided to prevent needle 32 from contacting other objects or personnel to thus avoid contamination or damage.

The invention can be used for blood collection from neonates or any other patient. Blood collection can be accomplished from arteries, veins, capillaries, or the umbilical cord. A preferred method of blood collection in accordance with the invention is described below.

In arterial, venous, or umbilical blood collection, needle assembly 16 is used. Plug 20 of end cap 14 on one end of capillary tube 12 (referred to as a "proximal end" below) is removed from opening 26 and hub 34 of needle assembly 16 is fitted over end cap 14 on the proximal end of capillary tube 12. Specifically, the Luer surface defined in hub 34 is frictionally mated with the Luer surface defined on the outer surface of base portion 18 of end cap 14 on the proximal end. Note that either end can be the proximal end because both end caps 14 of the preferred embodiment have Luer surfaces defined thereon. At any time prior to accessing a blood supply, as described below, plug 20 of end cap 14 of the end of capillary tube 12 opposite the proximal end (referred to as the "distal end" below) is removed from opening 26 to open the distal end of capillary tube 12.

A tip of needle 32 is then inserted in a conventional manner into blood supply B which is schematically illustrated in FIG. 3. Blood supply B can be an artery, a vein, an umbilical artery or an umbilical vein. Also, access to various blood vessels can be provided in advance by a catheter or other blood line, and blood supply B can be a proximal access port of the catheter or other blood line. Once blood supply B is accessed by needle 32, capillary tube 12 will begin to fill by drawing blood into passage 13 formed therethrough through capillary action (i.e. the movement of liquid due to the forces of adhesion, cohesion, and surface tension).

When passage 13 of capillary tube 12 is filled with blood, i.e. a sample of approximately 100 microliters has been collected in passage 13, needle 32 is withdrawn from blood supply B and plug 20 of end cap 14 on the distal end of capillary tube 12 is immediately placed in opening 26 to seal the distal end of capillary tube 12. Needle assembly 16 is then removed from end cap 14 of the proximal end of capillary tube 12 and plug 20 of end cap 14 of the proximal end is immediately placed in opening 26 to seal the proximal end of capillary tube 12. A 100 microliter sample is now sealed in passage 13 of capillary tube 12 as illustrated in FIG. 4. Note that access to blood supply B can be accomplished without needle assembly 16 by coupling a catheter or other blood line directly with the Luer surface defined on the outer surface of one of end caps 14. To collect blood from a capillary, end cap 14 on the proximal end is removed entirely. Note that a needle assembly is not used for capillary blood collection and thus the phrase "proximal end", as used herein, refers to an end of capillary tube 12 into which blood is drawn and does not necessarily require or infer that a needle or needle assembly be attached to that end. With plug 20 of end cap 14 of the distal end removed from opening 26, the exposed proximal end of capillary tube 12 is placed in the capillary blood flow. Access to capillary blood supply can be obtained using a standard well accepted capillary-puncture policy. Passage 13 formed through capillary tube 12 will then fill with blood due to capillary action. When passage 13 in capillary tube 12 has filled with blood, plug 20 of end cap 14 of the distal end of capillary tube 12 can be placed in opening 26 to seal the distal end of capillary tube 12. Immediately after removing the proximal end of capillary tube 12 from the capillary blood flow, end cap 14 having plug 20 inserted in opening 26 can be placed on the proximal end of capillary tube 12 to seal the proximal end of capillary tube 12.

It can be seen that the invention facilitates collection of blood. Particularly the use of end cap 14 having plug 20 and a Luer surface permits capillary tube 12 to be quickly and reliably sealed to minimize exposure of a collected blood sample to ambient air. The use of flexible arms 22 insures that stoppers are easily located and positioned. Further, the invention facilitates other handling procedures of the blood sample contained in sealed capillary tube 12, such as introducing the blood sample into a blood gas analyzer, or other test instrument. Preferred methods of introducing blood from capillary tube 12 into a test instrument are described below.

In the case of a test instrument having a female port, one end cap 14 is removed from capillary tube 12 and the exposed end of capillary tube 12 is inserted directly into the female port. While capillary tube 12 is maintained in position, plug 20 of the opposite end is removed from opening 26 allowing the blood to flow out of capillary tube 12 into the female port of the test instrument for analysis.

In the case of a test instrument having a male port, plug 20 of one end cap 14 is removed from opening 26 and the male sampler probe of the test instrument is introduced into passage 13 of capillary tube 12 through the unplugged opening 26. Plug 20 of the other end cap 14 is then removed from opening 26 so that the blood can be drawn from capillary tube 12 into the test instrument for analysis. Alternatively, one of end caps 14 can be removed entirely to provide access for the probe. Accordingly, the invention facilitates transferring a blood sample from capillary tube 12 into a test instrument while minimizing exposure of the blood sample to ambient air.

The capillary tube and the end caps can be made of any appropriate materials. The end caps can be attached to the capillary tube in any manner. If the end caps are permanently attached to the capillary tube, some flexibility of use may be lost and thus it is preferable that at least one of the end caps be removable from the capillary tube. The capillary tube can be of any size to accommodate the desired sample volume. The end caps on each end of the capillary tube can be identical or different from one another. Preferably, the blood collection instrument is entirely disposable. However, portions or the entirety thereof can be manufactured for sterilization and reuse.

The preferred embodiment relies entirely on capillary action to draw blood into the capillary tube. However, a small syringe, such as a tuberculin syringe, can be coupled to the distal end to provide aspiration, particularly for venous blood collection. Any type of suction device can be coupled to the distal end to facilitate aspiration. The capillary tube and the end caps can have any appropriate cross-sectional shape. Therefore, the term "tube", as used herein refers to an elongate hollow body of any cross-sectional shape.

The invention has been described through preferred embodiments. However, various modifications can be made without departing from the scope of the invention as defined by the appended claims.

What is claimed is:

1. A blood sample collection apparatus comprising:
   an elongated capillary tube having an open proximal end and an open distal end;
   a first end cap including a base portion having an inner end and an outer end and a passage extending between said inner end and said outer end, a plug configured to selectively close said passage and a Luer surface defined on an outer portion thereof, said inner end of said base portion being coupled to said proximal end of said capillary tube; and
   a second end cap coupled to said distal end of said capillary tube.

2. An apparatus as recited in claim 1, wherein said second end cap comprises a base portion having an inner end, an outer end and a passage extending between said inner end and said outer end, and a plug configured to selectively close said passage of said second end cap, said inner end of said second end cap being coupled to said distal end of said capillary tube.

3. An apparatus as recited in claim 2, wherein said plug of said first end cap and said plug of said second end cap are stoppers, said first end cap further comprises a flexible arm extending between said stopper of said first end cap and said base portion of said first end cap, said second end cap further comprises a flexible arm extending between said stopper of said first end cap and said base portion of said second end cap.

4. An apparatus as recited in claim 2, wherein said plug of said second end cap comprises a hydrophobic filter disposed in said passage of said base portion of said second end cap.

5. An apparatus as recited in claim 4, further comprising a visual indicator formed on said second end cap to indicate that said second end cap includes said hydrophobic filter.

6. An apparatus as recited in claim 2 wherein an outer portion of said second end cap has a Luer surface defined thereon.

7. An apparatus as recited in claim 2, further comprising a needle assembly including a hub and a needle coupled to said hub, said hub defining a mating Luer surface and being configured to mate with said Luer surface defined on said first end cap.

8. A blood sample collection method comprising the steps of:
   coupling a needle assembly having a needle to a first end cap on an open proximal end of an elongated capillary tube, the first end cap including a base portion having an inner end and an outer end and a passage extending between the inner end and the outer end, a first plug configured to selectively close the passage, and a Luer surface defined thereon, the inner end being coupled to the proximal end of the capillary tube, said coupling step including disposing a hub of the needle assembly over the Luer surface with the plug not closing the passage of the base portion of the first end cap;
   placing an end of the needle in communication with a blood supply;
   drawing blood through the needle and the passage into the capillary tube;

closing the distal end of the capillary tube with a second end cap;

removing the needle assembly from the capillary tube; and closing the passage of the first end cap with the plug.

9. A method as recited in claim 8 wherein said placing step comprises inserting the end of the needle into a blood vessel.

10. A method as recited in claim 8, wherein said placing step comprises inserting the end of the needle into a blood line.

11. A method as recited in claim 8, wherein said step of closing the distal end comprises placing a second plug in an opening of a passage formed through the second end cap, the second plug being attached to a base portion of the second end cap by a second flexible arm, and wherein said step of closing the passage of the first end cap comprises placing the first plug in an opening of the passage of the first end cap, the first plug being attached to the base portion of the first end cap by a first flexible arm.

12. A method as recited in claim 11, further comprising the steps of:

removing one of the first end cap and the second end cap from one of the proximal end and the distal end of the capillary tube;

inserting one of the proximal end and the distal end of the capillary tube into a female port of a test instrument; and analyzing the blood with the test instrument.

13. A method as recited in claim 11, further comprising the steps of:

opening the passage of one of the first end cap and the second end cap;

inserting a probe of a test instrument into the passage of the one of the first end cap and the second end cap; and analyzing the blood with the test instrument.

14. A blood sample collection method comprising the steps of:

coupling a needle assembly having a needle to a first end cap on an open proximal end of an elongated capillary tube, the first end cap including a base portion having an inner end and an outer end and a passage extending between the inner end and the outer end, a first plug configured to selectively close the passage, and a Luer surface defined thereon, the inner end being coupled to the proximal end of the capillary tube, said coupling step including disposing a hub of the needle assembly over the Luer surface with the plug not closing the passage of the base portion of the first end cap;

placing an end of the needle in communication with a blood supply;

drawing blood through the needle and the passage into the capillary tube;

removing the needle assembly from the capillary tube; and closing the passage of the first end cap with the plug and the distal end of the capillary tube with a second end cap.

15. A method as recited in claim 14, wherein said closing step comprises closing the passage with the first end cap prior to closing the distal end of the capillary tube with the second end cap.

16. A method as recited in claim 14, wherein said closing step comprises closing the passage with the first end cap subsequent to closing the distal end of the capillary tube with the second end cape.

17. A method as recited in claim 14 wherein said placing step comprises inserting the end of the needle into a blood vessel.

18. A method as recited in claim 14, wherein said placing step comprises inserting the end of the needle into a blood line.

19. A method as recited in claim 14, wherein said step of closing comprises closing the distal end by placing a second plug in an opening of a passage formed through the second end cap, the second plug being attached to a base portion of the second end cap by a second flexible arm, said step of closing further comprises closing the passage of the first end cap by placing the first plug in an opening of the passage of the first end cap, the first plug being attached to the base portion of the first end cap by a first flexible arm.

20. A method as recited in claim 14, further comprising the steps of:

removing one of the first end cap and the second end cap from one of the proximal end and the distal end of the capillary tube;

inserting one of the proximal end and the distal end of the capillary tube into a female port of a test instrument; and analyzing the blood with the test instrument.

21. A method as recited in claim 14 further comprising the steps of:

opening the passage of one of the first end cap and the second end cap;

inserting a probe of a test instrument into the capillary tube through the passage of the one of the first end cap and the second end cap; and analyzing the blood with the test instrument.

22. An end cap for closing an end of a capillary tube configured to retain a blood sample, said end cap comprising:

a base portion adapted to receive the end of the capillary tube, said base portion having a passage defined therethrough;

a plug configured to selectively close said passage; and a Luer surface defined on an outer portion of said base portion.

23. An end cap as recited in claim 22 wherein said plug comprises a stopper, said end cap further comprising a flexible arm extending between said stopper and said base portion.

24. An end cap as recited in claim 22 wherein said plug comprises a hydrophobic filter disposed in said passage.

25. An end cap for closing an end of a capillary tube configured to retain a blood sample, said end cap comprising:

a base portion having a passage defined therethrough;

a plug configured to selectively close said passage; and a Luer surface defined on an outer portion of said base portion;

wherein said plug comprises a stopper, said end cap further comprising a flexible arm extending between said stopper and said base portion.

26. An end cap for closing an end of a capillary tube configured to retain a blood sample, said end cap comprising:

a base portion having a passage defined therethrough;

a plug configured to selectively close said passage; and a Luer surface defined on an outer portion of said base portion;

wherein said plug comprises a hydrophobic filter disposed in said passage.

* * * * *